United States Patent [19]

Kawaguchi et al.

[11] 4,250,170
[45] Feb. 10, 1981

[54] ANTIBACTERIAL AGENTS BU-2349A AND B AND METHOD OF USING SAME

[75] Inventors: Hiroshi Kawaguchi, Tokyo; Masataka Konishi, Yokohama; Takashi Tsuno, Higashimurayama; Takeo Miyaki, Yokohama, all of Japan

[73] Assignee: Bristol-Myers Company, New York, N.Y.

[21] Appl. No.: 47,455

[22] Filed: Jun. 11, 1979

Related U.S. Application Data

[63] Continuation-in-part of Ser. No. 955,035, Oct. 26, 1978, abandoned.

[51] Int. Cl.$^3$ .................... A61K 31/71; C07H 15/22
[52] U.S. Cl. ........................................ 424/181; 536/1; 536/17 R; 435/80
[58] Field of Search ..................... 424/181; 536/17

[56] References Cited

U.S. PATENT DOCUMENTS

| 4,007,167 | 2/1977 | Martin et al. | 536/17 |
| 4,048,431 | 9/1977 | Hlavka et al. | 536/17 |
| 4,066,753 | 1/1978 | Hanesslan | 536/17 |
| 4,123,607 | 10/1978 | Hlavka et al. | 536/17 |

*Primary Examiner*—Johnnie R. Brown
*Attorney, Agent, or Firm*—David M. Morse

[57] ABSTRACT

A novel water-soluble basic antibiotic complex designated herein as Bu-2349 is produced by fermentation of Bu-2349-producing strains of the genus Bacillus. Complex Bu-2349 and its bioactive components designated as Bu-2349A and B are found to possess marked inhibitory activity against gram-positive and gram-negative bacteria including various types of aminoglycoside-resistant bacteria.

9 Claims, 5 Drawing Figures

INFRARED ABSORPTION SPECTRUM OF Bu-2349 A HYDROCHLORIDE

FIG. 2 INFRARED ABSORPTION SPECTRUM OF Bu-2349 B HYDROCHLORIDE

CLEAR MAGNETIC RESONANCE SPECTRUM OF Bu-2349 A HYDROCHLORIDE IN D₂O

NUCLEAR MAGNETIC RESONANCE SPECTRUM OF Bu-2349 B HYDROCHLORIDE IN D₂O

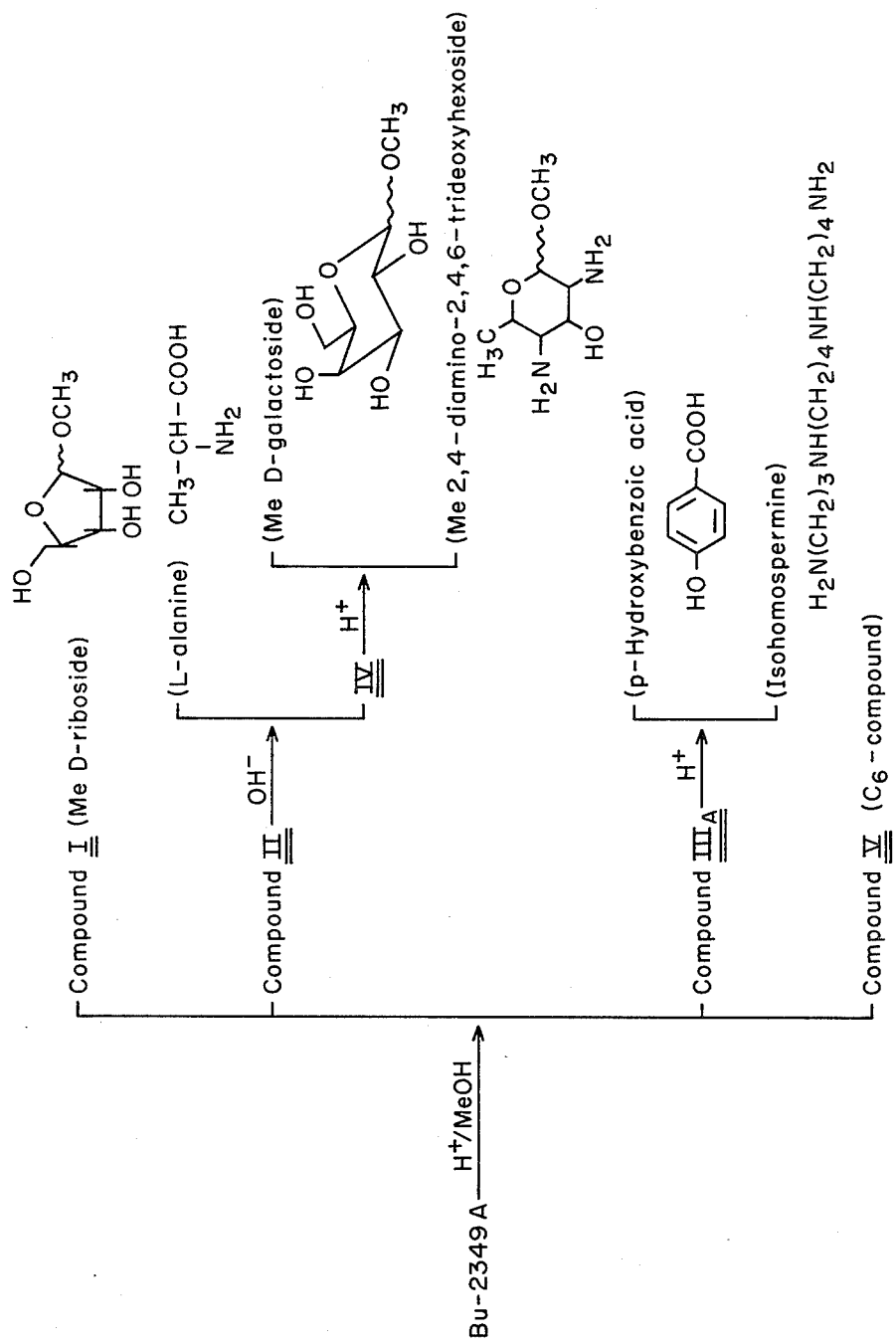
FIG. 5 STRUCTURAL CONSTITUENTS OF Bu-2349 A

ANTIBACTERIAL AGENTS BU-2349A AND B AND METHOD OF USING SAME

CROSS-REFERENCE TO RELATED APPLICATION

This is a continuation-in-part of co-pending application Ser. No. 995,035 filed Oct. 26, 1978, now abandoned.

BACKGROUND OF THE INVENTION

This invention relates to a new antibiotic complex and to its production, recovery and separation into two bioactive components.

2. Description of the Prior Art

Various aminoglycoside antibiotics such as kanamycin, gentamicin, streptomycin, neomycin, tobramycin, amikacin and paromomycin are known in the art. There exists a need, however, for additional new broad-spectrum antibiotics, particularly those having activity against aminoglycoside-resistant organisms.

U.S. Pat. No. 4,007,167 discloses the antibiotics BM-123$\gamma_1$ and BM-123$\gamma_2$ having the structures

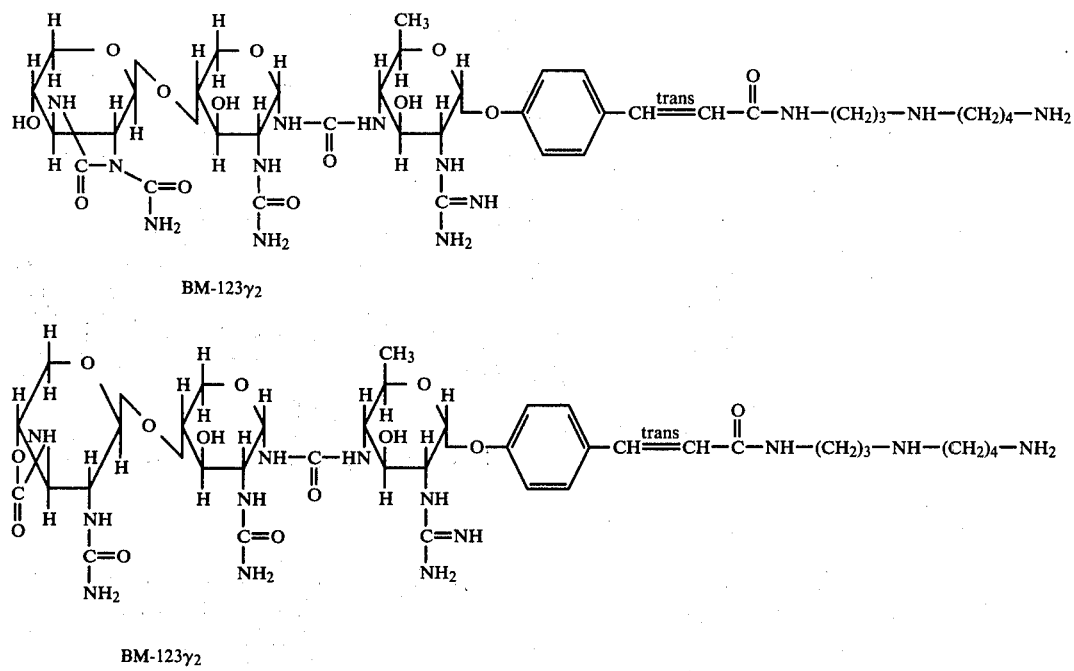

BM-123$\gamma_2$

BM-123$\gamma_2$

SUMMARY OF THE INVENTION

There is provided by the present invention a new water-soluble basic antibiotic complex designated Bu-2349, said complex being prepared by cultivating a Bu-2349-producing strain of the genus Bacillus, most preferably Bacillus sp. ATCC 31429 or Bacillus sp. ATCC 31430 or a mutant thereof, in an aqueous nutrient medium under submerged aerobic conditions until a substantial amount of Bu-2349 complex is produced by said organism in said culture medium and, optionally, recovering the Bu-2349 complex from the culture medium.

The invention also provides a process for producing as separate substances the bioactive antibiotic components of the Bu-2349 complex designated herein as Bu-2349A and B, said process comprising adsorbing the Bu-2349 complex on a cationic ion-exchange resin, fractionally eluting the Bu-2349 A and B components from the adsorbent and recovering the desired separated components.

The present invention includes within its scope the Bu-2349 complex and bioactive components Bu-2349 A and B in dilute forms, as crude concentrates and in purified forms. The new antibiotics may be provided as free bases or as acid addition salts with pharmaceutically acceptable organic or inorganic acids.

DESCRIPTION OF THE DRAWINGS

FIG. 5 shows the structural features of Bu-2349A.

DETAILED DESCRIPTION

Figure 1:
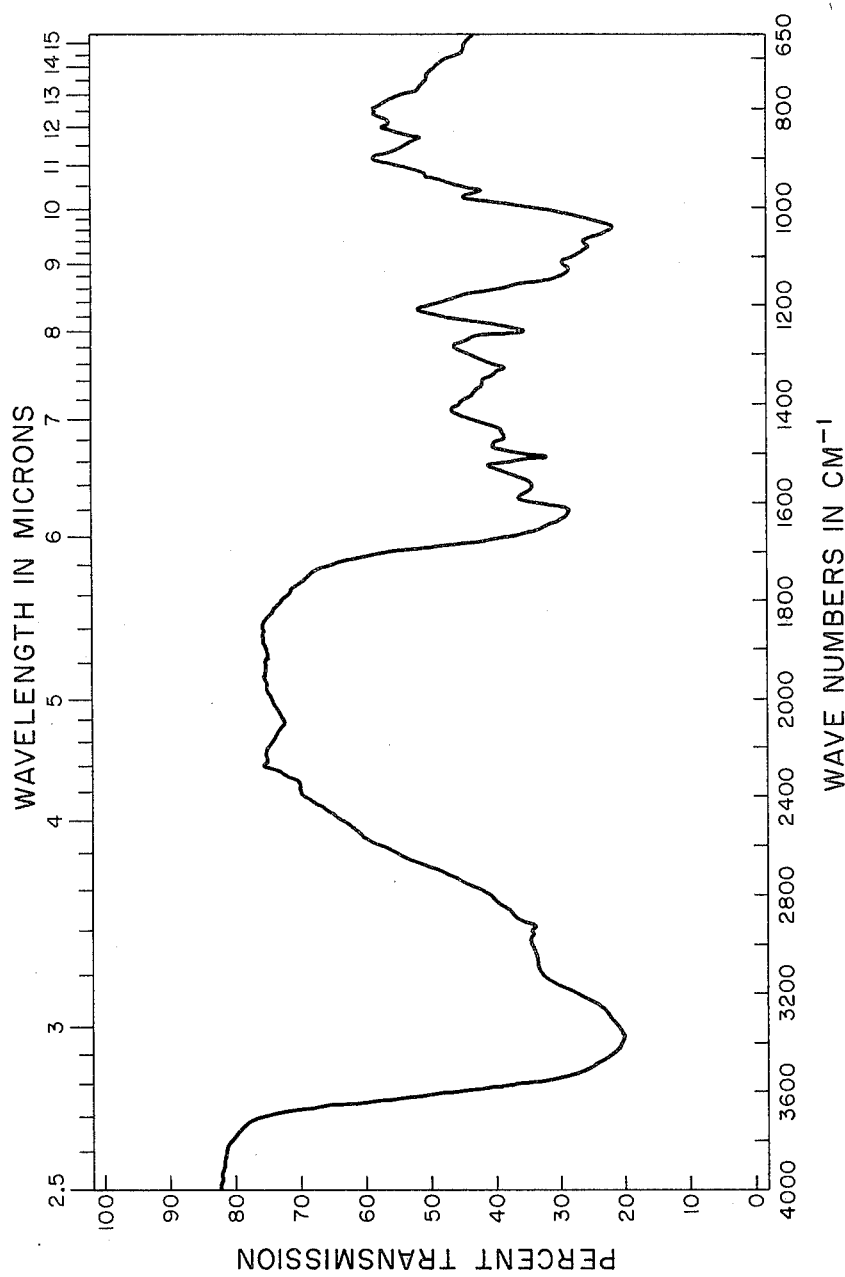
FIG. 1 shows the infrared absorption spectrum of Bu-2349A as the hydrochloride salt when pelleted in potassium bromide.

This invention relates to a novel aminoglycoside antibiotic complex designated herein as Bu-2349. The complex is produced by fermentation of a microorganism belonging to the genus Bacillus. Any strain belonging to the genus Bacillus and capable of forming Bu-2349 in culture medium may be used. The preferred producing organisms are designated Bacillus sp. strain F173-B61 and Bacillus sp. strain F262-B54 in the Bristol-Banyu culture collection. The above strains were isolated from soil samples collected in West Germany and India, respectively, and have been deposited with the American Type Culture Collection (ATCC), Rockville, Md., U.S.A., and added to their permanent collection of microorganisms as ATCC 31429 and ATCC 31430, respectively.

The novel aminoglycoside complex of this invention comprises two bioactive aminoglycoside components which have been arbitrarily designated as Bu-2349A and B. The complex and each of the above-mentioned components exhibit a broad spectrum of antibacterial activity and are thus valuable as antibacterial agents, as nutritional supplements in animal feeds and as therapeutic agents for animals. In particular, the new antibiotics are useful in the treatment of infectious diseases in mammals (including man) caused by gram-positive and gram-negative bacteria including such diseases attributed to aminoglycoside-resistant bacteria. Additionally, the antibiotics are useful in cleaning and sterilizing laboratory glassware and surgical instruments and may be used in combination with soaps, detergents and wash solutions for sanitation purposes.

THE BU-2349-PRODUCING MICROORGANISMS

The preferred Bu-2349-producing organisms designated Bacillus sp. strain F173-B61 (ATCC 31429) and Bacillus sp. strain F262-B54 (ATCC 31430) are aerobic, gram-positive, spore-forming rod bacteria and are thus classified as belonging to the genus Bacillus.

For the taxonomic study of the above-mentioned organisms, the methods described in Bergey's Manual, 8th Ed., 529-551 (1974) were used. As shown in Table 1, the morphological characteristics of strains F173-B61 and F262-B54 resemble those of *Bacillus cereus* or *Bacillus megaterium*. These four organisms possess the following characteristics in common: (1) positive gram-stain; (2) vegetative cells larger than those of *Bacillus subtilis* or related species; (3) sporangia not swollen at site of endospore; and (4) the presence of intracellular globules which are unstainable by fuchsin.

The morphological characteristics (Table 1) of *B. thuringiensis* and *B. anthracis* are closely related to cereusmegaterium. *B. thuringiensis* is pathogenic to larvae of Lepidoptera and forms intracellular protein crystals. *B. anthracis* is a causative organism of anthrax in man and animals, requires thiamine and many amino acids for growth and forms non-motile cells. On account of these properties, strains F173-B61 and F262-B54 are differentiated from *B. thuringiensis* or *B. anthracis*.

TABLE 1

Morphological Characteristics

| | Strain F173-B61 | Strain F262-B54 |
|---|---|---|
| Vegetative cells: | rod | rod |
| Width, μm | 1.0–1.2 | 1.0–1.2 |
| Length, μm | 1.6–4.4 | 2.4–4.0 |
| Motility | motile | motile |
| Spores: | | |
| Shape | oval | oval |
| Distension of sporangia at the site of spore | negative | negative |
| Position | central | central |
| Gram-stain | positive | positive |
| Intracellular globules unstainable by fuchsin | present | present |
| Intracellular protein crystals | absent | absent |

| | Bacillus cereus ATCC 10702 | Bacillus megaterium Bg-1 |
|---|---|---|
| Vegetative cells: | rod | rod |
| Width, μm | 1.0–1.2 | 1.0–1.2 |
| Length, μm | 2.4–4.0 | 1.6–3.2 |
| Motility | motile | motile |
| Spores: | | |
| Shape | oval | oval |
| Distension of sporangia | negative | negative |
| Position | central | central |
| Gram-stain | positive | positive |
| Intracellular globules unstainable by fuchsin | present | present |
| Intracellular protein crystals | absent | absent |

As shown in Table 2, strain F173-B61 differs from strain F262-B54 in its growth under anaerobic conditions, its positive egg-yolk reaction, nitrate reduction and Voges-Proskauer (VP) reaction. Thus, strain F173-B61 can be classified as *Bacillus cereus* while strain F262-B54 can be placed in *Bacillus megaterium* or a group of *Bacillus cereus/megaterium* intermediate strains as described by B. C. Knight, et al. in *J. Gen. Microbiol.* 4:508–538 (1950).

TABLE 2

Cultural and Physiological Characteristics

| | Strain F173-B61 | Strain F262-B54 |
|---|---|---|
| Cell mass grown in glucose nitrate broth & tryptosoy broth | floccose, sedimented & white; not viscous | floccose, sedimented & white; not viscous |
| Colony on nutrient agar (28° C., 6 days) | | |
| Color | pale yellow | pale yellow |
| Extreme | heaped, non-spreading | heaped, non-spreading |
| Surface | slightly rugose, pustular | slightly rugose, pustular |
| Size (mm in dia.) | 10~12 | 8~10 |
| Growth-temperature: | | |
| Abundant growth | 20~45° C. | 20~45° C. |
| No growth | 10° C., 50° C. | 10°·C., 50° C. |
| Acid in glucose broth | + | + |
| Gas from glucose | − | − |
| Acid from arabinose, xylose and mannitol | − | − |
| Anaerobic growth in Hugh & Leifson medium | + | − |
| Growth in 0.001%-lysozyme | + | + |
| Nitrite from nitrate | + | − |
| Egg-yolk reaction | + | − |
| Acetoin from glucose | + | variable |

TABLE 2-continued

| Cultural and Physiological Characteristics | | |
|---|---|---|
| Gelatin liquefaction | + | + |
| Hydrolyses of starch & casein | + | + |
| Alkali on citrate salts agar | + | + |
| Catalase | + | + |
| Growth at 7% sodium chloride | + | + |
| Growth in ammonium salts medium | + | + |
| Requirement of vitamin or amino acid for growth | − | − |

| | Bacillus cereus ATCC 10702 | Bacillus megaterium Bg-1 |
|---|---|---|
| Cell mass grown in glucose nitrate broth & tryptosoy broth | floccose, sedimented & white; not viscous | floccose, sedimented & white; not viscous |
| Colony on nutrient agar (28° C., 6 days) | | |
| Color | pale yellow | pale yellow |
| Extreme | diffused, root-like outgrowth | heaped, non-spreading |
| Surface | dull, frosted glass appearance | slightly rugose, pustular |
| Size (mm in dia.) | 18~24 | 6~8 |
| Growth-temperature: | | |
| Abundant growth | 20~45° C. | 20~45° C. |
| No growth | 10° C., 50° C. | 10° C., 50° C. |
| Acid in glucose broth | + | + |
| Gas from glucose | − | − |
| Acid from arabinose, xylose and mannitol | − | − |
| Anaerobic growth in Hugh & Leifson medium | + | − |
| Growth in 0.001%-lysozyme | + | − |
| Nitrite from nitrate | + | + |
| Egg-yolk reaction | + | − |
| Acetoin from glucose | + | − |
| Gelatin liquefaction | + | + |
| Hydrolyses of starch & casein | + | + |
| Alkali on citrate salts agar | + | + |
| Catalase | + | + |
| Growth at 7% sodium chloride | + | + |
| Growth in ammonium salts medium | + | + |
| Requirement of vitamin or amino acid for growth | − | − |

It is to be understood that for the production of Bu-2349 the present invention, though described in detail with reference to the specific Bacillus strains F173-B61 and F262-B54, is not limited to these microorganisms or to microorganisms fully described by the cultural characteristics disclosed herein. It is intended that the invention also include other Bu-2349-producing strains or mutants of the preferred strains which can be produced by methods known in the art, for example, by subjecting the disclosed microorganisms to x-ray or ultraviolet radiation, nitrogen mustard, phage exposure, and the like.

PREPARATION OF THE ANTIBIOTICS

The Bu-2349 antibiotics are produced by conventional fermentation methods by cultivating a Bu-2349-producing strain of the genus Bacillus, most preferably Bacillus sp. ATCC 31429 or ATCC 31430 or a mutant thereof, under submerged aerobic conditions in an aqueous nutrient medium. The organism is grown in a nutrient medium containing an assimilable carbon source, for example an assimilable carbohydrate. Examples of preferred carbon sources include glucose, fructose, mannose, glycerol and the like. The nutrient medium should also contain an assimilable nitrogen source such as, for example, fish meal, soybean meal, peptones, etc. Nutrient inorganic salts may also be advantageously incorporated in the culture medium and such salts may comprise any of the conventionally used salts capable of providing sodium, potassium, ammonium, calcium, phosphate, sulfate, chloride, bromide, nitrate, carbonate or like ions.

Production of the Bu-2349 complex can be effected at any temperature conducive to satisfactory growth of the organism, e.g. 20°–45° C., and is most preferably carried out at a termperature of about 28°–30° C. Ordinarily, optimum production is obtained in about 4–6 days. A neutral or near neutral initial pH is preferably employed in the medium. For preparation of relatively small amounts, shake flasks and surface culture can be employed, but for the preparation of large amounts, submerged aerobic culture in sterile tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermenting medium. Further agitation in tanks is provided by a mechanical impeller. An antifoaming agent such as lard oil may be added as needed.

The production of Bu-2349 in the fermentation medium can readily be followed during the course of the fermentation by a paper disc-agar diffusion assay using Bacillus subtilis PCI 219 as the test organism.

ISOLATION AND PURIFICATION OF BU-2349

After optimum broth potency has been obtained (as determined, for example, by the assay procedure mentioned above), the broth is made neutral or slightly acidic (e.g. pH~6.5) and the mycelium and undissolved residues are separated from the broth by conventional means such as filtration or centrifugation. The antibiotic activity is in the filtrate and may be recovered therefrom by employing conventional adsorption techniques used for water-soluble basic antibiotics. The adsorbents which can be employed most advantageously are the cation exchange resins, for example weakly acidic cation exchange resins of the carboxylic acid type (e.g. a resin of the type available commercially under the tradename "Amberlite IRC-50"). The filtrate is passed through a column packed with the resin, for example Amberlite IRC-50 in the ammonium form, and the column is then developed with water, 0.1 N $NH_4OH$ and 1 N $NH_4OH$ solutions, successively. The antibacterial fractions eluted by 1 N $NH_4OH$ are pooled and concentrated in vacuo to yield Bu-2349 complex.

SEPARATION OF COMPONENTS BU-2349A AND B

The Bu-2349 complex may be separated into Bu-2349A and B by use of a cationic exchange resin, for example a chromatographic grade resin of the "Amberlite CG-50" (tradename, produced by Rohm & Haas Co.) type in the ammonium form. The complex after being dissolved in water is applied to the resin and eluted gradiently with 0.2 N, 0.5 N and 1 N $NH_4OH$. Bu-2349B is eluted first with 0.5 N $NH_4OH$ and the Bu-2349A comes off the column later with 1 N $NH_4OH$ solution. When the two preferred Bacillus strains are used, Bu-2349A is the major component and the Bu-2349B the minor component.

The separated antibiotic components may be subjected to further purification as by chromatography over a cation exchange resin (e.g. Amberlite CG-50 in the ammonium form) or a gel filtration agent. Preferred gel filtration agents are the cross-linked dextran gels such as "Sephadex LH-20" produced by Pharmacia Fine Chemicals AB, Uppsala, Sweden.

CHARACTERIZATION DATA FOR BU-2349 ANTIBIOTIC COMPONENTS

Bu-2349A and B in the form of their hydrochloride salts are white amorphous solids. Both substances are soluble in water, slightly soluble in methanol, ethanol, dimethylsulfoxide and dimethylformamide and practically insoluble in other common organic solvents. They give positive reactions with ninhydrin, anthrone, Molisch, Fehling and Remini reagents, and negative reactions with $FeCl_3$ and Sakaguchi reagents.

Bu-2349A hydrochloride has no definite melting point and decomposes above 215° C. Similarly, Bu-2349B has no definite melting point and decomposes above 224° C.

Bu-2349A and B hydrochlorides have the following approximate percentage elemental compositions:

Bu-2349A hydrochloride: C, 44.48; H, 7.34; N, 8.37; Cl, 6.44; O (by difference), 33.37.

Bu-2349B hydrochloride: C, 43.55; H, 6.92; N, 8.06; Cl, 6.64; O (by difference), 34.83.

The molecular weight of the N-pentacetyl derivative of Bu-2349A was determined to be 1100 by vapor pressure osmometry. The molecular formula of Bu-2349A free base is $C_{44}H_{75}N_7O_{18}$.

The specific rotations of the hydrochloride salts are as follows:

$[\alpha]_D^{22} = +109°$ (c 1.0, $H_2O$) for Bu-2349A $[\alpha]_D^{22} = +115°$ (c 1.0 $H_2O$) for Bu-2349B.

Bu-2349A and B hydrochlorides may be differentiated from each other by their $R_f$ values in silica gel thin layer chromatography using the following solvent systems:

| Solvent System | | Bu-2349A | Bu-2349B |
|---|---|---|---|
| chloroform:methanol:28% ammonium hydroxide:$H_2O$ (1:4:2:1 v/v) | $R_f$ | 0.27 | 0.50 |
| methanol:10% ammonium acetate (1:1 v/v) | | 0.14 | 0.31 |
| methyl acetate:n-propanol: 28% ammonium hydroxide (45:105:60 v/v) | | 0.06 | 0.16 |

The ultraviolet absorption spectrum of Bu-2349A in water exhibits a single absorption maximum at 247 nm($E_{1cm}^{1\%}$ 131) which does not shift in acidic or alkaline media. Bu-2349B also shows an absorption maximum at 247 nm ($E_{1cm}^{1\%}$ 148) with no pH shift.

Figure 2:
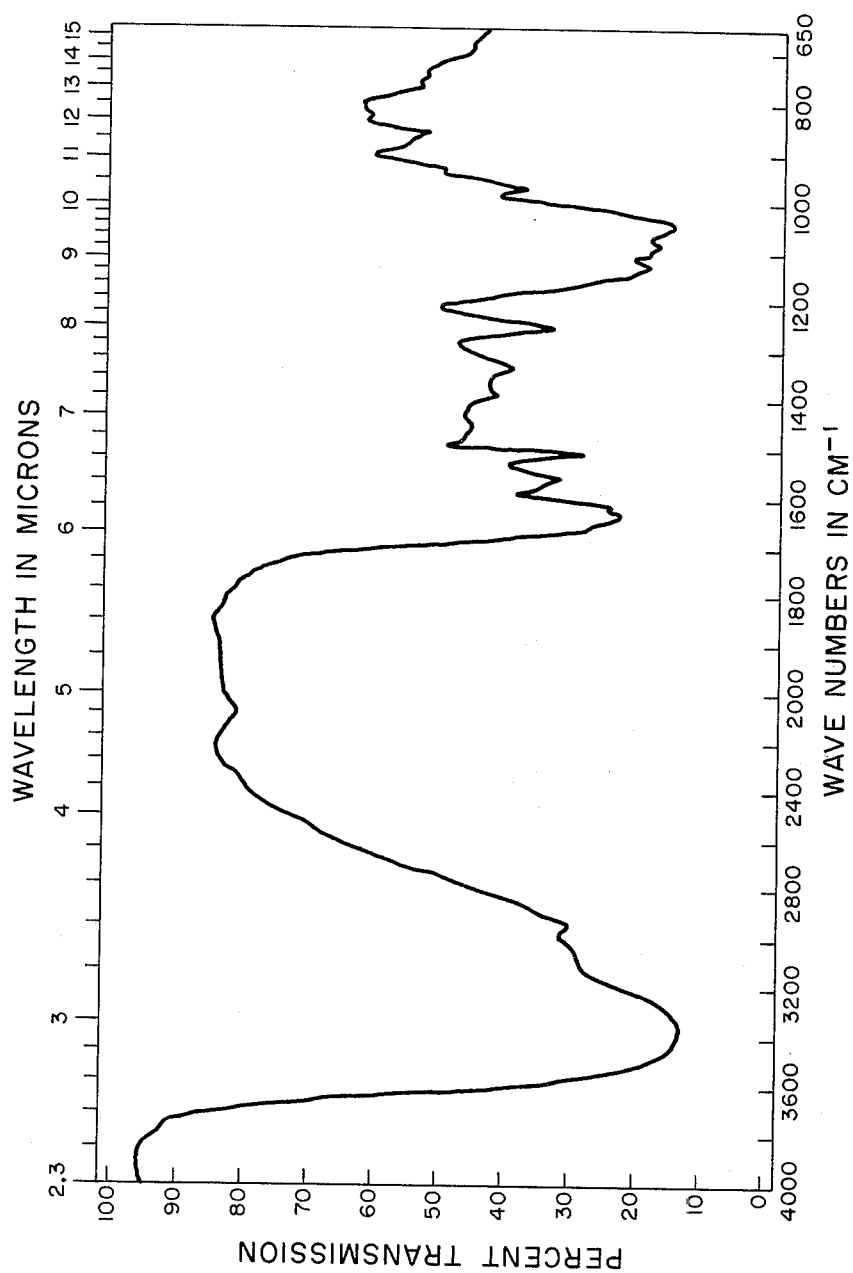
FIG. 2 shows the infrared absorption spectrum of Bu-2349B as the hydrochloride salt when pelleted in potassium bromide.

The infrared absorption spectra of Bu-2349A and B hydrochlorides (measured in KBr) are shown in FIG. 1 and FIG. 2, respectively. Amide carbonyl at 1630 $cm^{-1}$ and polyhydroxy groups at around 3400 and 1040 $cm^{-1}$ are indicated.

Figure 3:
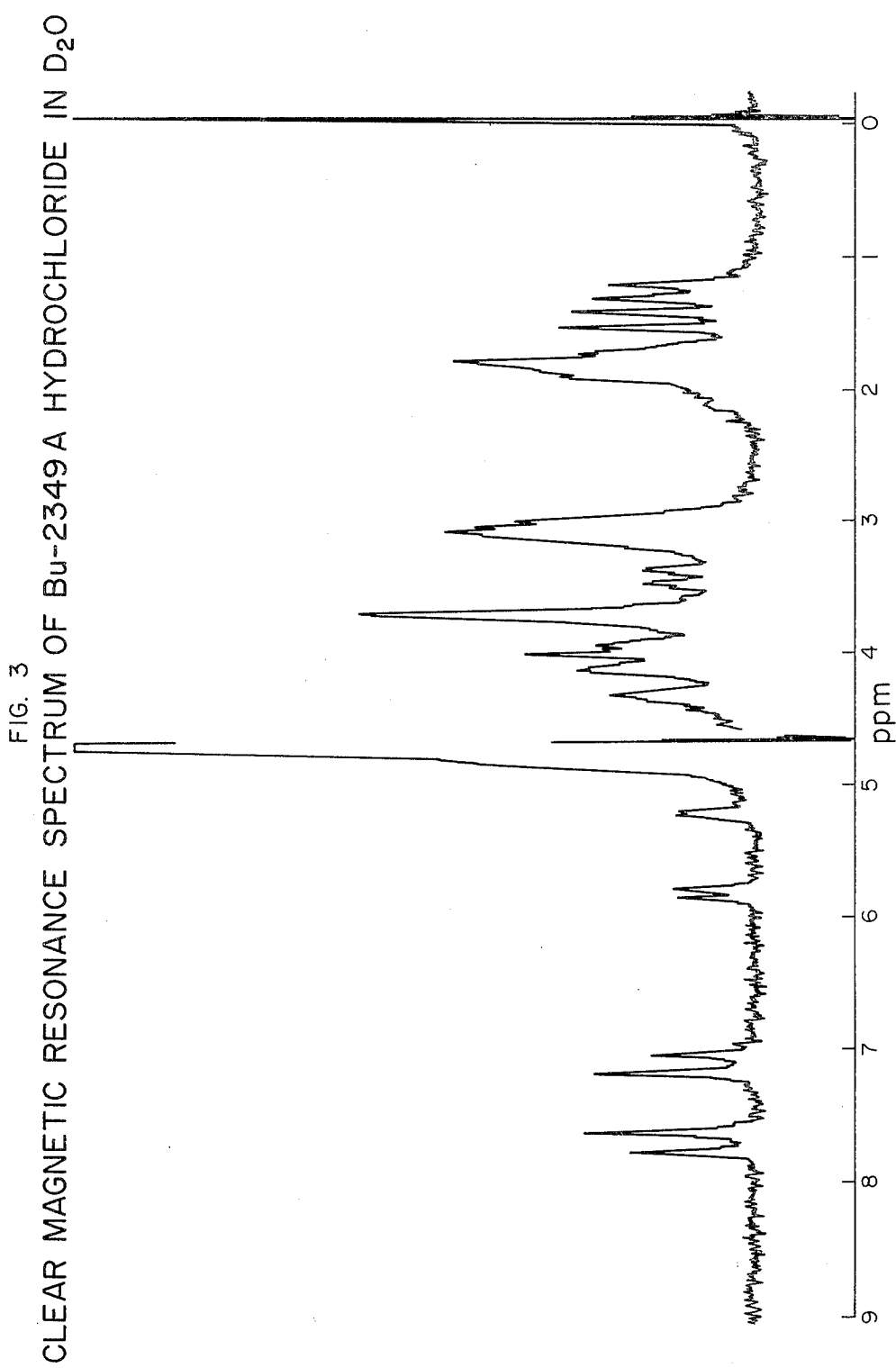
FIG. 3 shows the proton magnetic resonance spectrum of Bu-2349A as the hydrochloride salt dissolved in $D_2O$ using TMS as the external standard as determined with a JEOL 60 MHz NMR spectrometer (type TNM-C-60HL).
Figure 4:
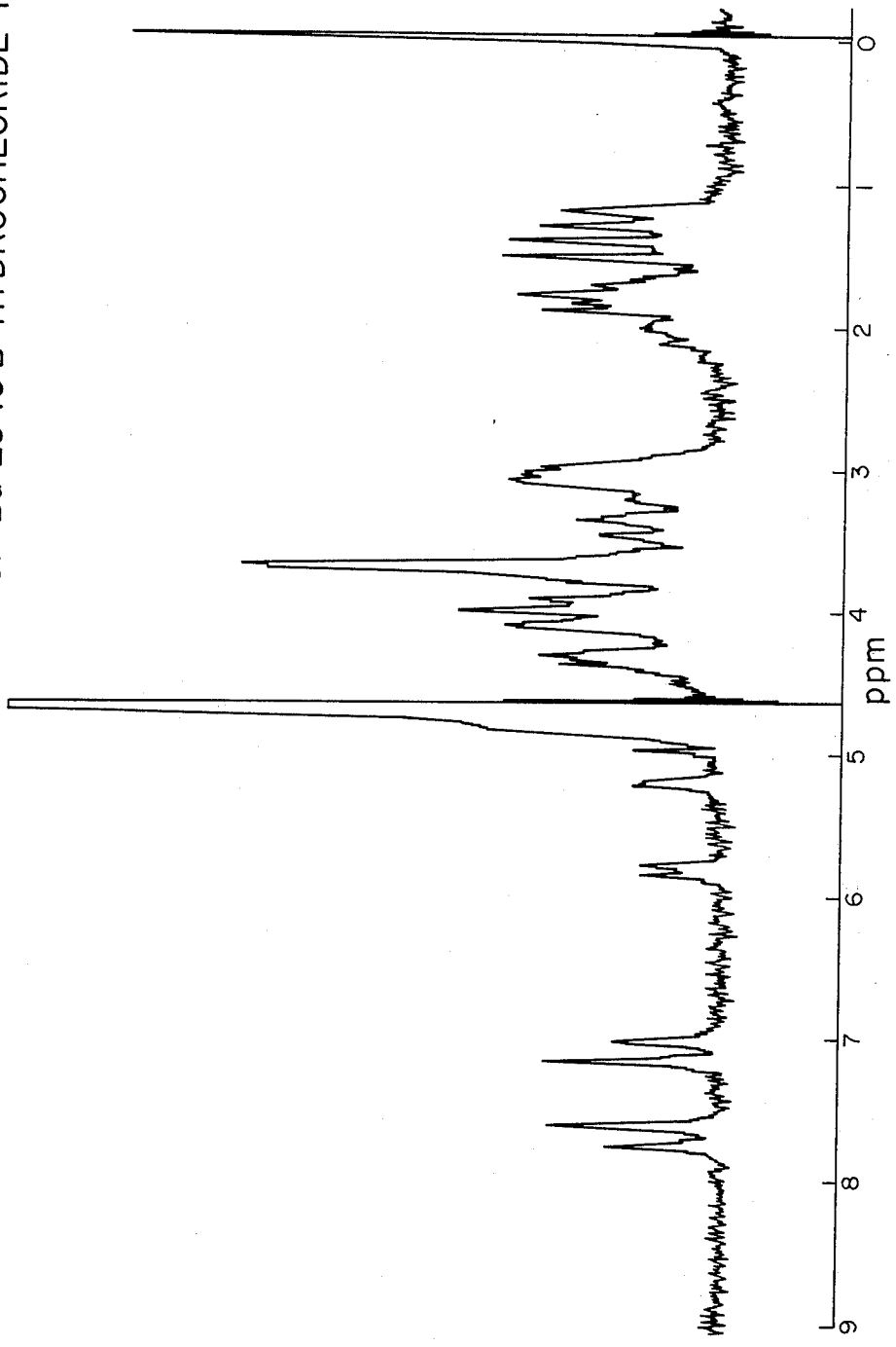
FIG. 4 shows the proton magnetic resonance spectrum of Bu-2349B as the hydrochloride salt dissolved in $D_2O$ using TMS as the external standard as determined with a JEOL 60 MHz NMR spectrometer (type TNM-C-60HL).

The NMR spectra of Bu-2349A and B hydrochlorides are shown in FIGS. 3 and 4, respectively.

Bu-2349A and B are basic substances capable of forming salts with acids, and pharmaceutically acceptable acid addition salts of the antibiotics are included within the present invention. "Pharmaceutically acceptable" salts are salts in which the toxicity of the compound as a whole in warm-blooded animals is not increased relative to the non-salt form. Examples of suitable pharmaceutically acceptable acid addition salts include those salts formed by standard reaction with both organic and inorganic acids such as hydrochloric, sulfuric, phosphoric, acetic, succinic, citric, lactic, maleic, fumaric, palmitic, formic, stearic, propionic, tartaric, benzoic, salicylic, methanesulfonic, benzenesulfonic, cinnamic and the like. As an example of salt formation, the free base compounds may be dissolved in water, treated with the desired acid and then lyophilized. For purposes of the present invention the free base forms of the antibiotics are equivalent to the pharmaceutically acceptable acid addition salts.

STRUCTURAL FEATURES OF Bu-2349
Components

The $^{13}C$ nuclear magnetic resonance spectrum of Bu-2349A indicated the presence of 44 carbons including two methyl and two carbonyl carbons. Both of the methyl groups appeared as a doublet ($\delta$1.27 and 1.49 ppm) in the proton NMR spectrum (FIG. 3). The NMR also indicated the presence of four aromatic protons (AB quartets, $\delta$7.10 and 7.70 ppm) and five anomeric or double bond protons at around $\delta$4.7~5.9 ppm.

When heated under reflux with 0.5 N methanolic hydrogen chloride, Bu-2349A was split into three fragments, I, II and III$_4$. Fragment I was identified as methyl D-riboside. Alkaline hydrolysis (0.1 N Ba(OH)$_2$, 100° C., 18 hours) of II yielded L-alanine and a disaccharide (IV) containing two primary amino groups. The N-diacetyl derivative of compound IV was hydrolyzed with methanolic HCl to give methyl D-galactoside and an unidentified basic sugar moiety which is assumed to be 2,4-diamino-2,4,6-trideoxyhexose from the mass and NMR spectral data. The NMR spectra of II and IV suggested that the alanine carbonyl group should join with the C-2 amino group of the diaminosugar moiety in compound II. The basic fragment III$_A$ was isolated as a crystalline hydrochloride, m.p. 252° C.

Anal. Calc'd. for $C_{18}H_{32}N_4O_2.3HCl$: C, 48.49; H, 7.91; N, 12.57; Cl, 23.86. Found: C, 48.48; H, 7.96; N, 12.46; Cl, 23.97. Mass: m/e 336 (M+), 278, 247, 207, 186, 121, etc. $\lambda_{max}^{H2O}$ 252 nm ($\epsilon$13,960), $\lambda_{max}^{0.1\ N\ HCl}$ 252 nm ($\epsilon$13,960) and $\lambda_{max}^{0.1\ N\ NaOH}$ 289 nm ($\epsilon$20,380). On refluxing with 6 N HCl, III$_A$ was cleaved into p-hydroxybenzoic acid and a novel amino compound, $C_{11}H_{28}N_4$, whose structure was determined to be N-($\delta$-aminobutyl)-N'-($\gamma$-aminopropyl)-1,4-diaminobutane (designated as isohomospermine). The mass and NMR analyses of III$_A$ indicated that the terminal amino function of the aminopropyl part of the isohomospermine moiety was acylated by p-hydroxybenzoic acid. Fragment III$_A$ thus has the structure

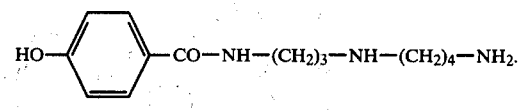

As mentioned above, the $^{13}$C-NMR spectrum of Bu-2349A indicated the presence of 44 carbons in the antibiotic molecule. The three fragments (I, II and III$_A$) isolated from the acid hydrolyzate of Bu-2349A accounted for 38 carbons of the antibiotic. Therefore, Bu-2349A should contain another constituent (designated as V) with six carbons which was deduced to be a sugar or related substance by $^{13}$C and proton NMR analyses.

The structural features of Bu-2349A described above are summarized in FIG. 5. This component contains L-alanine, p-hydroxybenzoic acid, D-galactose, D-ribose, 2,4-diamino-2,4,6-trideoxyhexose, N-($\delta$-aminobutyl)-N'-($\gamma$-aminopropyl)-1,4-diaminobutane and a compound with a six carbon skeleton. Component Bu-2349B contains the same constituents as Bu-2349A except that the N-($\delta$-aminobutyl)-N'-($\gamma$-aminopropyl)-1,4-diaminobutane is replaced by spermidine.

Subsequent study has shown the six carbon sugar moiety mentioned above to be 6-deoxy-$\alpha$-D-xylo-hex-5-enopyranose having the formula

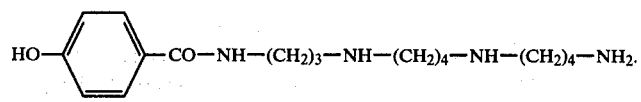

From the foregoing data the partial structure of Bu-2349A may be represented as

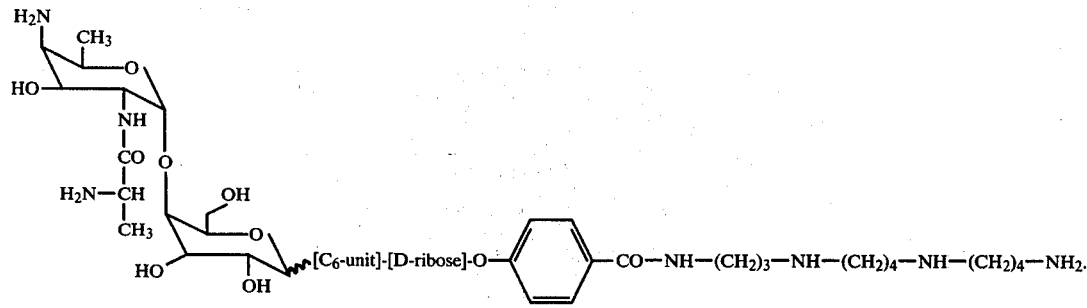

Acid hydrolysis of Bu-2349B gave three fragments I, II and III$_B$. Fragments I and II were identical with those isolated from Bu-2349A. Fragment III$_B$ showed physico-chemical properties similar to III$_A$ and its molecular formula was determined to be $C_{14}H_{23}N_3O_2$. On acid hydrolysis with 6 N HCl, III$_B$ was cleaved into p-hydroxybenzoic acid and spermidine ($C_7H_{19}N_3$). Fragment III$_B$ thus has the structure

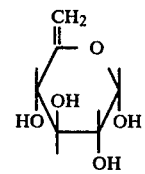

Based on the above work, the structures of Bu-2349A and Bu-2349B have been determined to be

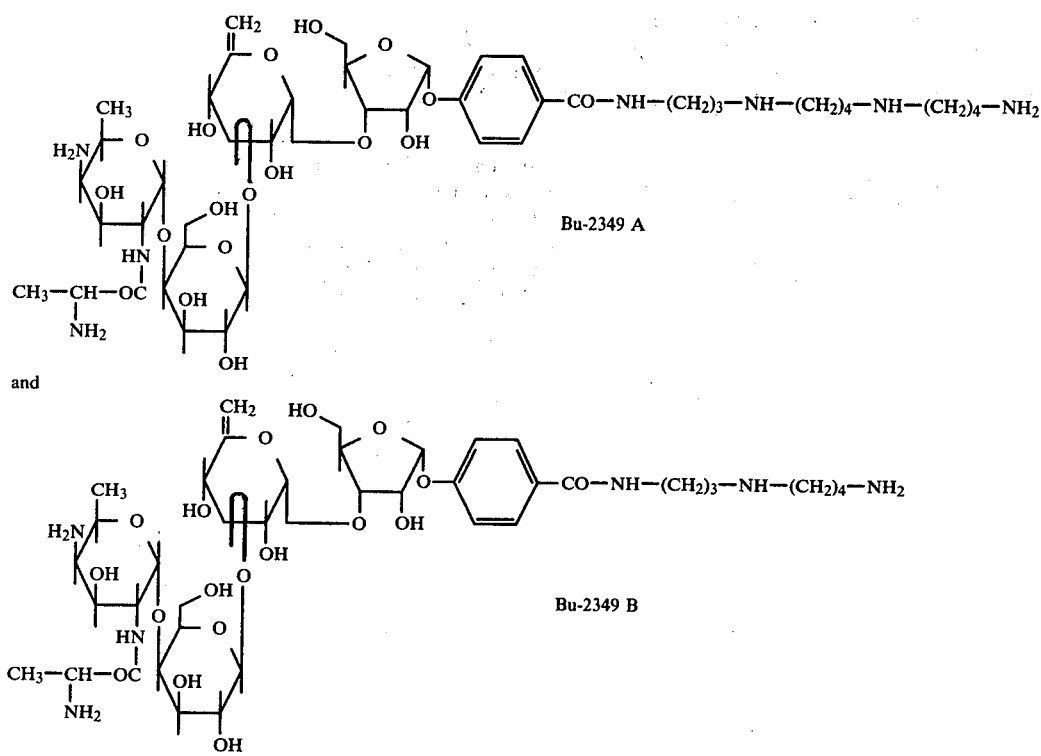

Bu-2349 A

Bu-2349 B

BIOLOGICAL PROPERTIES

The minimum inhibitory concentrations (MIC) of Bu-2349A and B were determined against a wide variety of bacteria by the two-fold agar dilution method. Mueller-Hinton agar medium was generally used for the determination of bacterial MIC except for species of Streptococcus, Neisseria and Hemophilus for which Gonococcus agar medium (GC agar, Nissui Co., Tokyo) was used. Gifu anaerobe agar medium (GAM agar, Eiken Co., Tokyo) was used for anaerobic bacteria. The MIC's were determined after overnight incubation at 37° C. with an initial inoculum equivalent to a $10^{-4}$ dilution of an 18-hour culture for the aerobic and anaerobic bacteria, except for Streptococcus, Neisseria and Hemophilus for which a $10^{-2}$ dilution was used. As shown in Table 3, Bu-2349A and B are active against gram-positive and gram-negative bacteria including those which produce various types of aminoglycoside-modifying enzymes. Bu-2349A was inactive against most of the anaerobic organisms tested (Table 4).

TABLE 3

In Vitro Activity of Bu-2349 Against Aerobic Bacteria

| BBRI Code | Test Organisms | Enzyme* | MIC (mcg./ml.) | |
|---|---|---|---|---|
| | | | Bu-2349A** | Bu-2349B*** |
| Sa-1 | Staphylococcus aureus 209P | | 3.1 | 12.5 |
| Sa-2 | Staphylococcus aureus Smith | | 3.1 | 12.5 |
| Sa-33 | Staphylococcus aureus Terajima | | 1.6 | 6.3 |
| Sa-77 | Staphylococcus aureus | ANT(4') | 12.5 | 50 |
| Si-2 | Staphylococcus epidermidis | ANT (4') | 3.1 | 25 |
| Bs-1 | Bacillus subtilis PCI 219 | | 1.6 | 25 |
| Sp-3 | Streptococcus pyogenes | | >100 | >100 |
| Sv-1 | Streptococcus viridans | | >100 | >100 |
| Dp-4 | Streptococcus pneumoniae | | >100 | >100 |
| M6-1 | Mycobacterium 607 | | 3.1 | 12.5 |
| Mp-1 | Mycobacterium phlei D88 | | 3.1 | 25 |
| Mr-1 | Mycobacterium ranae ATCC 110 | | 3.1 | 25 |
| Ec-1 | Escherichia coli NIHJ | | 1.6 | 3.1 |
| Ec-3 | Escherichia coli Juhl | | 1.6 | 6.3 |
| Ec-5 | Escherichia coli ML-1630 | APH(3')—1 | 1.6 | 6.3 |
| Ec-9 | Escherichia coli | AAC(6')—1 | 0.8 | 0.8 |
| Ec-49 | Escherichia coli | APH(3')—2 | 1.6 | 3.1 |
| Ec-62 | Escherichia coli | AAC(3)—1 | 1.6 | 12.5 |
| Ec-72 | Escherichia coli | ANT(2'') | 1.6 | 6.3 |
| El-35 | Enterobacter cloacae | AAC(3)—3 | 3.1 | 12.5 |
| Kp-2 | Klebsiella pneumoniae | | 3.1 | 12.5 |
| Kp-33 | Klebsiella pneumoniae | AAC(3)—3 | 3.1 | 12.5 |
| Pm-1 | Proteus mirabilis | | 6.3 | 25 |

TABLE 3-continued
In Vitro Activity of Bu-2349 Against Aerobic Bacteria

| BBRI Code | Test Organisms | Enzyme* | MIC (mcg./ml.) Bu-2349A** | MIC (mcg./ml.) Bu-2349B*** |
|---|---|---|---|---|
| Pg-1 | Proteus morganii | | 25 | 100 |
| Pv-1 | Proteus vulgaris | | 1.6 | 6.3 |
| Pr-2 | Proteus rettgeri | | 0.8 | 3.1 |
| Ps-2 | Proteus stuartii | AAC(2') | 1.6 | 1.6 |
| Sm-2 | Serratia marcescens | | 25 | 50 |
| Pa-3 | Pseudomonas aeruginosa | | 25 | 100 |
| Nm-1 | Neisseria meningitidis | | >100 | >100 |
| Ng-1 | Neisseria gonorrhoeae | | >100 | >100 |
| He-2 | Hemophylus influenzae | | >100 | >100 |

*aminoglycoside-modifying enzymes produced
**lot 113-1-62
***lot 113-1-2242

TABLE 4
In Vitro Activity of Bu-2349A Against Anaerobic Bacteria (GAM Medium, pH 7)

| BBRI Code | Test Organism | MIC in mcg./ml. |
|---|---|---|
| Bf-1 | Bacteroides fragilis | >100 |
| Bf-3 | Bacteroides fragilis | >100 |
| Bf-7 | Bacteroides fragilis | >100 |
| Sn-1 | Sphaerophorus necrophorus | >100 |
| Fv-1 | Fusobacterium varium ATCC 8501 | >100 |
| Vp-1 | Veillonella parvula ATCC 17745 | >100 |
| Ae-1 | Acidoaminococcus fermentans ATCC 25085 | 50 |
| Ch-1 | Clostridium chauvoei | >100 |
| Cp-1 | Clostridium perfringens | >100 |
| Pc-102 | Propionibacterium acnes | 12.5 |
| Pb-1 | Peptostreptococcus anaerobium B43 | >100 |
| Pe-101 | Peptococcus aerogenes ATCC 14963 | >100 |

The influence of inoculum size on MIC was tested on Mueller-Hinton agar using an inoculum of $10°$, $10^{-2}$ or $10^{-4}$ dilution of the overnight culture of test organisms. As shown in Table 5, changes in inoculum size had no significant effect on the antibiotic activity of Bu-2349A.

TABLE 5
Effect of Inoculum Size on MIC of Bu-2349A (Mueller-Hinton Agar, pH 7)

| BBRI Code | Test Organism | MIC (mcg./ml.) $10^{-4}$ dil. | $10^{-2}$ dil. | $10^0$ dil. |
|---|---|---|---|---|
| Sa-1 | S. aureus 209P | 3.1 | 3.1 | 6.3 |
| Sa-63 | S. aureus | 6.3 | 6.3 | 12.5 |
| Bs-1 | B. subtilis PCI 219 | 3.1 | 3.1 | 6.3 |
| Ec-3 | E. coli Juhl | 3.1 | 3.1 | 6.3 |
| Ec-5 | E. coli ML-1630 | 3.1 | 3.1 | 6.3 |
| Pa-3 | P. aeruginosa | 25 | 50 | >50 |
| Kp-2 | K. pneumoniae | 3.1 | 6.3 | 12.5 |
| Pm-1 | P. mirabilis | 12.5 | 25 | 50 |
| Pg-1 | P. morganii | 25 | 50 | >50 |
| Pv-3 | P. vulgaris | 6.3 | 6.3 | 12.5 |

The effect of media pH on the MIC's of Bu-2349A was determined at three pH levels (6, 7 and 8) using Mueller-Hinton agar. As shown in Table 6, Bu-2349A showed much reduced activity at pH 6 as compared with that determined at pH 7. It was approximately twice as active at pH 8 than at pH 7.

TABLE 6
Effect of pH on MIC of Bu-2349A (Mueller-Hinton Agar, Inoculum Size: $10^{-4}$ Dilution)

| BBRI Code | Test Organism | MIC (mcg./ml.) pH 6 | pH 7 | pH 8 |
|---|---|---|---|---|
| Sa-1 | S. aureus 209P | 50 | 3.1 | 1.6 |
| Sa-63 | S. aureus | >50 | 6.3 | 3.1 |
| Bs-1 | B. subtilis PCI 219 | 50 | 3.1 | 1.6 |
| Ec-3 | E. coli Juhl | 25 | 3.1 | 1.6 |
| Ec-5 | E. coli ML-1630 | 50 | 3.1 | 1.6 |
| Pa-3 | P. aeruginosa | >50 | 25 | 12.5 |
| Kp-2 | K. pneumoniae | 50 | 3.1 | 3.1 |
| Pm-1 | P. mirabilis | >50 | 12.5 | 12.5 |
| Pg-1 | P. morganii | >50 | 25 | 25 |
| Pv-3 | P. vulgaris | >50 | 6.3 | 6.3 |

The media effect on the MIC's of Bu-2349A was tested using four kinds of assay media: Mueller-Hinton agar (MHA), nutrient agar (NA), heart infusion agar (HIA) and brain heart infusion agar (BHIA). The pH was adjusted at 7 and a $10^{-4}$ dilution of overnight culture was used for the inoculum. As shown in Table 7, Bu-2349A showed higher activity in NA and HIA than in MHA or BHIA.

TABLE 7
Effect of Medium on MIC of Bu-2349A (pH 7, Inoculum Size: $10^{-4}$ Dilution)

| BBRI Code | Test Organism | MIC (mcg./ml.) MHA* | NA | HIA | BHIA |
|---|---|---|---|---|---|
| Sa-1 | S. aureus 209P | 3.1 | 1.6 | 1.6 | 3.1 |
| Sa-63 | S. aureus | 6.3 | 6.3 | 3.1 | 6.3 |
| Bs-1 | B. subtilis PCI 219 | 3.1 | 0.8 | 1.6 | 6.3 |
| Ec-3 | E. coli Juhl | 3.1 | 3.1 | 1.6 | 6.3 |
| Ec-5 | E. coli ML-1630 | 3.1 | 1.6 | 1.6 | 3.1 |
| Pa-3 | P. aeruginosa | 50 | 6.3 | 12.5 | 25 |
| Kp-2 | K. pneumoniae | 3.1 | 1.6 | 1.6 | 3.1 |
| Pm-1 | P. mirabilis | 6.3 | 3.1 | 6.3 | 12.5 |
| Pg-1 | P. morganii | 25 | 6.3 | 25 | 25 |
| Pv-3 | P. vulgaris | 3.1 | 1.6 | 1.6 | 3.1 |

*MHA: Mueller-Hinton agar
NA: Nutrient agar
HIA: Heart infusion agar
BHIA: Brain heart infusion agar The in vivo antibacterial activity of Bu-2349A was determined by experimental infections in mice. Mice were challenged via the intraperitoneal route with a 100 X $LD_{50}$ dose of the pathogens in a 5% suspension of hog gastric mucin (American Laboratories, Omaha, Neb.). Bu-2349A was administered by the intramuscular route immediately after the bacterial challenge. A group of five mice was used for each dosage level and the animals were observed for five days to determine the median protective dose ($PD_{50}$). As shown in Table 8, Bu-2349A showed good protection against systemic lethal infections with S. aureus, E. coli, K. pneumoniae,

*P. vulgaris* and *P. mirabilis*. It was, however, inactive against the *S. pneumoniae* infection as was the case in the in vitro testing.

TABLE 8

In vivo activity of Bu-2349A By Intramuscular Administration

| Test Organism | PD$_{50}$ (mg./kg., im) |
|---|---|
| S. aureus Smith | 3.2 |
| E. coli Juhl | 5.4 |
| K. pneumoniae A9977 | 7.2 |
| S. pneumoniae A20759 | >100 |
| P. vulgaris A9436 | 12 |
| P. mirabilis A9554 | 16 |

Blood levels were determined in mice following intramuscular administration of Bu-2349A at a dose of 50 mg./kg. Blood samples were collected from orbital sinuses and assayed by the paper disc-agar plate method using *B. subtilis* PCI 219 as the test organism. The results are shown in Table 9. The peak blood level of Bu-2349A was obtained after 15 minutes, with rapid elimination from the blood stream thereafter. No antibiotic activity was detected after 2 hours.

TABLE 9

Mouse Blood Level of Bu-2349A (im, 50 mg./kg.)

| Time after administration | Blood level |
|---|---|
| 15 minutes | 15 mcg./ml. |
| 30 minutes | 12 |
| 60 minutes | 2.8 |
| 120 minutes | >1.0 |

The acute intramuscular and intravenous LD$_{50}$'s of Bu-2349A determined in mice were 315 mg./kg. and 35 mg./kg., respectively.

USE OF THE ANTIBIOTICS

As can be seen from the biological data presented above, Bu-2349 complex and its bioactive components Bu-2349 A and B possess marked inhibitory activity both in vitro and in vivo against gram-positive and gram-negative bacteria (including aminoglycoside-resistant bacteria) and are thus useful as antibacterial agents in human and veterinary medicine.

According to one aspect of the invention, there is provided a method for therapeutically treating an animal (including especially humans and other mammals) host affected by a bacterial infection which comprises administering to said host an effective antibacterial dose of Bu-2349A or Bu-2349B, or a mixture thereof, or a pharmaceutically acceptable acid addition salt thereof.

According to another aspect of the invention, a pharmaceutical composition is provided which comprises a therapeutically effective antibacterial amount of Bu-2349A or B, or a mixture thereof, or a pharmaceutically acceptable acid addition salt thereof, in combination with a pharmaceutical carrier or diluent. Such compositions are preferably administered by injection, although other routes of administration may be employed if desired.

The dosage of the antibiotic substances will vary with the form of administration and the particular substance chosen. Furthermore it will vary with the particular situs, host and disease being treated. Many factors that modify the action of the drug will be taken into account by the physician or veterinarian, for example, age, body weight, sex, diet, time of administration, route of administration, rate of excretion, condition of the patient, drug combinations, reaction sensitivities and severity of the disease. A parenteral dosage range of about 2-15 mg./kg. of body weight/day in divided doses (e.g. 2-3 times per day) is generally convenient for starting treatment. Optimum dosage under the particular circumstances may readily be determined by those skilled in the art.

For cleaning and disinfecting purposes, 0.1-10% solutions of the substances in water may be employed.

The following examples are provided for illustrative purposes only and are not intended to limit the scope of the invention. "Amberlite IRC-50" and "CG-50" mentioned in the examples are tradenames for weakly acidic cationic exchange resins of the carboxylic acid type. "Sephadex LH-20" is a tradename of a modified alkylated dextran gel filtration agent.

EXAMPLE 1

Fermentation of Complex

A well-grown agar slant of a strain of Bacillus species, F262-B54 (ATCC 31430), was used to inoculate vegetative medium containing 1% glucose, 0.5% yeast extract and 1% polypeptone, the pH being adjusted to 7.2 before sterilization. The seed culture was incubated at 28° C. for 24 hours on a rotary shaker (250 rpm), and 5 ml. of the culture was transferred to a 500-ml. Erlenmeyer flask containing 100 ml. of the fermentation medium composed of 3% glycerol, 0.5% soybean meal, 1% fish meal, 0.1% $(NH_4)_2SO_4$, 0.3% NaCl and 0.6% $CaCO_3$, the pH being adjusted to 7.2 before sterilization. The fermentation was carried out on a rotary shaker at 28° C. for 5-6 days. The activity of the antibiotic complex in the fermentation broth was determined by a paper disc-agar diffusion assay using *Bacillus subtilis* PCI 219 as the test organism. The antibiotic production reached a maximum of 100~150 mcg./ml. after 4~6 days.

EXAMPLE 2

Isolation and Purification

The fermented broth (45 L.) was adjusted to pH 6.5 with oxalic acid, stirred for 30 minutes and filtered with filter aid. The filtrate was passed through a column of "Amberlite IRC-50" ($NH_4^+$ form, 4.5 L), and the column was developed with water (45 L.), 0.1 N $NH_4OH$ and 1 N $NH_4OH$ solutions, successively. Antibacterial fractions eluted by 1 N $NH_4OH$ were pooled and concentrated in vacuo to yield a mixture of Bu-2349A and B (6.0 g.).

EXAMPLE 3

Separation of Components

For the separation and purification of the A and B components of Bu-2349, the crude complex (5 g.) was applied on a column of "Amberlite CG-50" ($NH_4^+$ form, 1 L.) which was eluted gradiently with 0.2 N, 0.5 N and 1 N $NH_4OH$. Bu-2349B (150 mg.) was eluted first with 0.5 N $NH_4OH$ and major component Bu-2349A (900 mg.) then eluted with 1 N $NH_4OH$ solution. Bu-2349A thus isolated was further purified by chromatography on "Sephadex LH-20" (250 ml.) with elution by aqueous methanol to yield the white carbonate salt of Bu-2349A (800 mg.). Bu-2349B was chromatographed in a similar way to obtain 110 mg. of the carbonate salt. Bu-2349A hydrochloride was prepared by dissolving the carbonate in water, adjusting to pH 4.0 with 0.1 N HCl and lyophilizing.

EXAMPLE 4

A well-known agar slant of Bacillus sp. F173-B61 (ATCC 31429) was used to inoculate vegetative medium containing 1% glucose, 0.5% yeast extract and 1% polypeptone, the pH being adjusted to 7.2 before sterilization. The seed culture was incubated at 28° C. for 24 hours on a rotary shaker (250 rpm) and 5 ml. of the culture was transferred to a 500 ml. Erlenmeyer flask containing 100 ml. of a fermentation medium composed of 2% glycerol, 1% corn steep liquor, 1% Pharmamedia (cottonseed meal), 0.3% $(NH_4)_2SO_4$, 0.003% $ZnSO_4.7H_2O$ and 0.4% $CaCO_3$, the pH being adjusted to 7.2 before sterilization. The fermentation was carried out on a rotary shaker at 28° C. for 5 days, at which time the antibiotic assay of the broth showed a potency of about 20 mcg./ml. The fermented broth is then isolated, purified and separated into the hydrochloride salts of Bu-2349A and B by the procedures of Examples 2 and 3.

Bu-2349A and B acid addition salts may be converted to the corresponding free bases by conventional procedures, e.g. ion exchange chromatography or neutralization of their aqueous solutions.

This invention is capable of industrial application.

We claim:

1. The antibiotic Bu-2349A having the formula

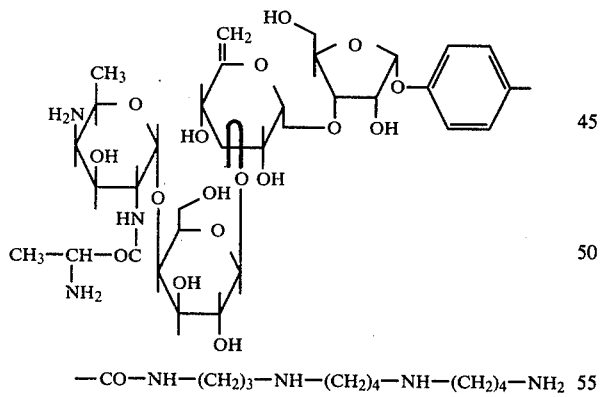

—CO—NH—$(CH_2)_3$—NH—$(CH_2)_4$—NH—$(CH_2)_4$—$NH_2$ or a pharmaceutically acceptable acid addition salt thereof.

2. The compound of claim 1 which is Bu-2349A free base.

3. The compound of claim 1 which is Bu-2349A hydrochloride.

4. The compound of claim 1 which is Bu-2349A carbonate.

5. The antibiotic Bu-2349B having the formula

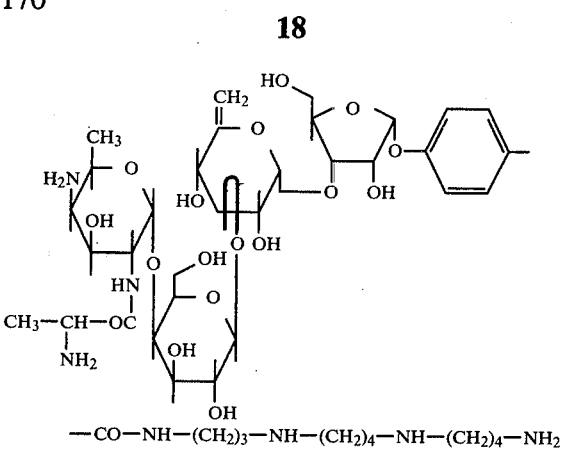

—CO—NH—$(CH_2)_3$—NH—$(CH_2)_4$—NH—$(CH_2)_4$—$NH_2$ or a pharmaceutically acceptable acid addition salt thereof.

6. The compound of claim 5 which is Bu-2349B free base.

7. The compound of claim 5 which is Bu-2349B hydrochloride.

8. The compound of claim 5 which is Bu-2349B carbonate.

9. A method for inhibiting the growth of pathogenic bacteria in an animal which comprises parenterally administering to said animal an effective antibacterial amount of an antibiotic selected from the group consisting of Bu-2349A having the formula

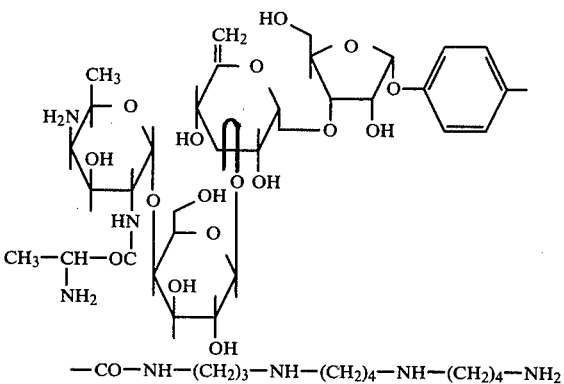

—CO—NH—$(CH_2)_3$—NH—$(CH_2)_4$—NH—$(CH_2)_4$—$NH_2$

Bu-2349B having the formula

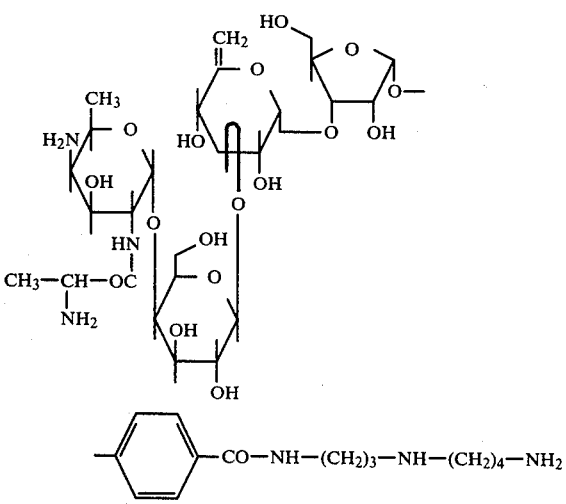

—CO—NH—$(CH_2)_3$—NH—$(CH_2)_4$—$NH_2$ and a pharmaceutically acceptable acid addition salt of Bu-2349A or B.

* * * * *

UNITED STATES PATENT AND TRADEMARK OFFICE
CERTIFICATE OF CORRECTION

PATENT NO. : 4,250,170
DATED : February 10, 1981
INVENTOR(S) : Hiroshi Kawaguchi, et al.

It is certified that error appears in the above—identified patent and that said Letters Patent is hereby corrected as shown below:

In column 18, line 15, "$-CO-NH-(CH_2)_3-NH-(CH_2)_4-NH-(CH_2)_4-NH_2$" should read -- $-CO-NH-(CH_2)_3-NH-(CH_2)_4-NH_2$ --.

Signed and Sealed this

Nineteenth Day of May 1981

[SEAL]

Attest:

RENE D. TEGTMEYER

Attesting Officer — Acting Commissioner of Patents and Trademarks